(12) United States Patent
Kanayama et al.

(10) Patent No.: US 9,448,234 B2
(45) Date of Patent: Sep. 20, 2016

(54) THERAPEUTIC AGENT FOR PRETERM DELIVERY OR ABORTION USING PLASMINOGEN ACTIVATOR INHIBITOR-1

(71) Applicant: National University Corporation Hamamatsu University School of Medicine, Shizuoka (JP)

(72) Inventors: Naohiro Kanayama, Shizuoka (JP); Kazuo Umemura, Shizuoka (JP); Takayuki Iwaki, Shizuoka (JP); Tetsumei Urano, Shizuoka (JP); Kotomi Ikuma, Shizuoka (JP)

(73) Assignee: NATIONAL UNIVERSITY CORPORATION HAMAMATSU UNIVERSITY SCHOOL OF MEDICINE, Shizuoka (JP)

( * ) Notice: Subject to any disclaimer, the term of this patent is extended or adjusted under 35 U.S.C. 154(b) by 64 days.

(21) Appl. No.: 14/358,116

(22) PCT Filed: Nov. 15, 2012

(86) PCT No.: PCT/JP2012/007348
§ 371 (c)(1),
(2) Date: May 14, 2014

(87) PCT Pub. No.: WO2013/073191
PCT Pub. Date: May 23, 2013

(65) Prior Publication Data
US 2014/0315227 A1    Oct. 23, 2014

(30) Foreign Application Priority Data

Nov. 15, 2011 (JP) .................................. 2011-249523

(51) Int. Cl.
| | | |
|---|---|---|
| *G01N 33/53* | (2006.01) | |
| *G01N 33/543* | (2006.01) | |
| *G01N 33/68* | (2006.01) | |
| *A61K 38/57* | (2006.01) | |
| *C07K 14/81* | (2006.01) | |

(52) U.S. Cl.
CPC ......... *G01N 33/54306* (2013.01); *A61K 38/57* (2013.01); *C07K 14/8132* (2013.01); *G01N 33/689* (2013.01); *G01N 2333/8132* (2013.01); *G01N 2800/368* (2013.01)

(58) Field of Classification Search
None
See application file for complete search history.

(56) References Cited

U.S. PATENT DOCUMENTS 5,420,016 A * 5/1995 Boguslaski .............. C12Q 1/04
                                                  106/2
2008/0107644 A1   5/2008 Fleenor et al.
2010/0286053 A1   11/2010 Kuan et al.
2011/0306058 A1   12/2011 Van Dreden et al.

FOREIGN PATENT DOCUMENTS

| CN | 1882357 A | 12/2006 |
|---|---|---|
| CN | 101605907 A | 12/2006 |
| CN | 101588798 A | 11/2009 |
| JP | 2010508306 A | 3/2010 |
| JP | 2010510793 A | 4/2010 |
| JP | 2011-172486 A | 9/2011 |
| WO | 0237120 A2 | 5/2002 |

OTHER PUBLICATIONS

Declerck et al., Measurement of Plasminogen Activator Inhibitor 1 in Biologic Fluids With a Murine Monoclonal Antibody-Based Enzyme-Linked Immunosorbent Assay, Blood, vol. 71, No. 1, Jan. 1988, pp. 220-225.*
Palmieri et al., Plasminogen Activator Inhibitor-1 and -3 Increase Cell Adhesion and Motility of MDS-MB-435 Breast Cancer Cells, The Journal of Biochemical Chemistry, vol. 277, No. 43, Oct. 25, 2002, pp. 40950-40957.*
Urano, Teisumei. "Fibrinolytic System." Japanese College of Angiology, Oct. 3, 2011, vol. 51/No. 3, 293-299 (English translation of abstract included).
Palomba, et al. "Plasminogen activator inhibitor 1 and miscarriage after metformin treatment and laparoscopic ovarian drilling in patients with polycystic ovary syndrome." Fertility and Sterility, Sep. 2005, vol. 84/No. 3, 761-765.
Phillippe, et al. "Expression of Coagulation-Related Protein Genes During LPS-Induced Preterm Delivery in the Pregnant Mouse." Reproductive Sciences, Jun. 21, 2011, vol. 18/No. 11, 1071-1079.
Asahina, et al. "Congenital Blood Coagulation Factor XIII Deficiency and Successful Deliveries: A Review of the Literature." Obstetrical and Gynecological Survey, 2007, vol. 62/No. 4, 255-260.
Binder, et al. "The plasminogen activator inhibitor 'paradox' in cancer." Immunology Letters, May 2, 2008, vol. 118, 116-124.
Fay, et al. "Brief Report: Complete Deficiency of Plasminogen-Activator Inhibitor Type 1 Due to a Frame-Shift Mutation." The New England Journal of Medicine, Dec. 10, 1992, vol. 327/No. 24, 1729-1733.
Iwaki, et al. "Life-threatening hemorrhage and prolonged wound healing are remarkable phenotypes manifested by complete plasminogen activator inhibitor-1 deficiency in humans." Journal of Thrombosis and Haemostasis, Jun. 6, 2011, vol. 9, 1200-1206.

(Continued)

*Primary Examiner* — Gary W Counts
(74) *Attorney, Agent, or Firm* — Pearne & Gordon LLP

(57) ABSTRACT

A method for diagnosing a risk for preterm delivery or miscarriage in a pregnant woman and preventing preterm delivery or miscarriage in the pregnant woman who has been determined to have the risk is provided. The method includes measuring plasminogen activator inhibitor-1 activity or level in plasma isolated from a pregnant woman. The method also includes determining that the pregnant woman has a risk for preterm delivery or miscarriage when the activity or the level is lower than that in the plasma of a normal pregnant woman. The method also includes administering plasminogen activator inhibitor-1 to the pregnant woman who has been determined to have the risk. A kit for the diagnosis of the degree of risk for preterm delivery or miscarriage also is provided. A pharmaceutical composition for the prevention of preterm delivery or miscarriage, comprising plasminogen activator inhibitor-1, also is provided.

11 Claims, 1 Drawing Sheet

(56) References Cited

OTHER PUBLICATIONS

Iwaki, et al. "Maternal Fibrinogen is Necessary for Embryonic Development." Current Drug Targets, 2005, vol. 6/No. 5, 535-539.

Meltzer, et al. "The Impact of the Fibrinolytic System on the Risk of Venous and Arterial Thrombosis." Seminars in Thrombosis and Hemostasis, 2009, vol. 35/No. 5, 468-477.

Asahina, et al. "Studies on the Role of Adhesive Proteins in Maintaining Pregnancy." Horm Res, 1998;50(suppl 2), 37-45.

Iwaki, et al. "Fibrinogen Stabilizes Placental-Maternal Attachment During Embryonic Development in the Mouse." American Journal of Pathology, vol. 160/No. 3, Mar. 2002, 1021-1034.

Pihusch, et al. "Plasminogen activator inhibitor-1: a review," Journal of Laboratory Medicine, 2005, vol. 29, No. 6, pp. 403-411.

Office Action and Search report issued in corresponding Japanese application No. 2013-544140, dated Jun. 2, 2015.

Gris, et al., Use of a Low-Molecular Weight Heparin (Enoxaparin) or of a Phenformin-like Substance (Moroxydine Chloride) in Primary Early Recurrent Aborters with an Impaired Fibrinolytic Capacity; Thrombosis and Haemostasis, 1995, vol. 73, No. 3, pp. 362-367.

Gris, et al., Plasma fibrinolytic activators and their inhibitors in women suffering from early recurrent abortion of unknown etiology; Journal of Laboratory and Clinical Medicine, 1993, vol. 122 No. 5, pp. 606-615.

Technical Data Sheet, AlphaLISA Research Reagents, Human plasminogen activator inhibitor-1 (PAI-1) kit; PerkinElmer Inc., Aug. 22, 2011, pp. 1-12 (author unknown).

Extended European search report issued in European Application No. 12849895.3, dated Jul. 3, 2015.

Tanaka, et al., Inactivation of plasminogen activator inhibitor type1 by activated factor XII plays a role in the enhancement of fibrinolysis by contact factors in-vitro, Life Sciences, 2009, vol. 85, pp. 220-225, Elsevier.

Office Action and Search report issued in corresponding Chinese Application No. 201280055808.9, dated Jan. 4, 2015.

\* cited by examiner

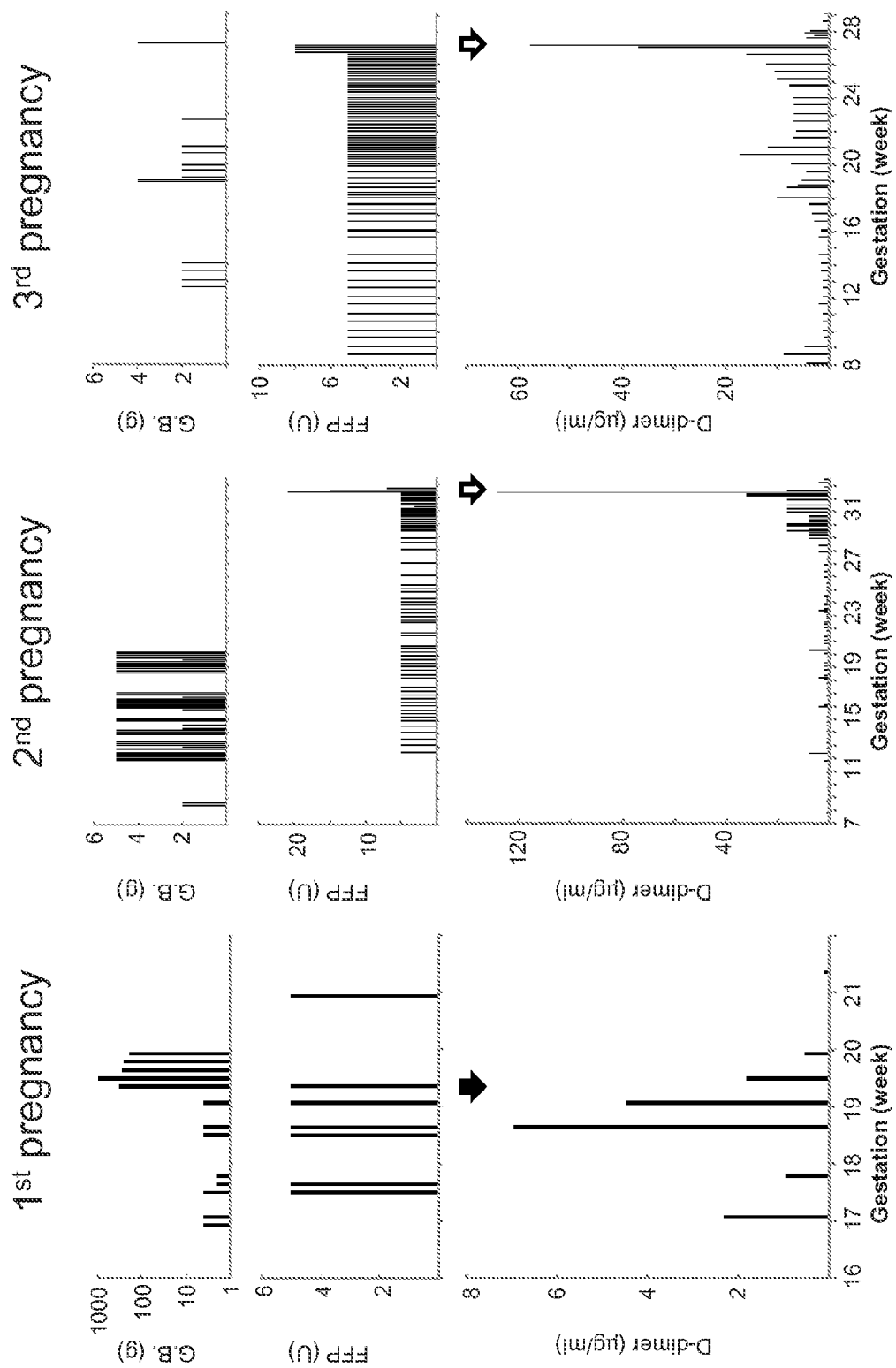

THERAPEUTIC AGENT FOR PRETERM DELIVERY OR ABORTION USING PLASMINOGEN ACTIVATOR INHIBITOR-1

TECHNICAL FIELD

The present invention relates to a method for diagnosing the degree of risk for preterm delivery or miscarriage, comprising measuring plasminogen activator inhibitor activity or level in plasma. Specifically, the present invention relates to: a method for diagnosing the degree of risk for preterm delivery or miscarriage, wherein when the plasminogen activator inhibitor activity or level is lower than those of normal pregnant woman, the degree of risk for preterm delivery or miscarriage is determined to be high; a kit for the diagnosis of the degree of risk for preterm delivery or miscarriage; and a pharmaceutical composition for the prevention of preterm delivery or miscarriage, comprising plasminogen activator inhibitor-1.

BACKGROUND ART

Subchorionic hematoma is known as a leading cause of preterm delivery and miscarriage. Although diagnostic imaging based on ultrasonic tomography is currently performed for subchorionic hematoma, no hematological diagnosis or treatment method has been established yet. Thus, once subchorionic hematoma occurs and progresses, preterm delivery and miscarriage cannot be avoided.

Plasminogen activator inhibitor-1 (PAI-1) is a member of the serine protease inhibitor (SERPIN) superfamily and is the primary physiological regulator of urokinase type plasminogen activator and tissue type plasminogen activator. Although a number of studies have indicated that elevated levels of PAI-1 are associated with several pathological states such as arterial thrombotic events (Non Patent Literature 1) and poor prognosis in cancer patients (Non Patent Literature 2), our knowledge of the consequences of PAI-1 deficiency is still limited due to the rarity of this condition. The present inventors have recently reported a case of genetically identified complete PAI-1 deficiency in a human (Non Patent Literature 3). The patient showed a tendency for massive bleeding, which was also observed in a PAI-1-deficient patient in the previous report (Non Patent Literature 4).

Genetic alterations that lead to a predisposition for bleeding are associated with clinical complications during pregnancy. The most vivid example of this association is congenital afibrinogenemia and congenital coagulation factor XIII (FXIII) deficiency, which result in genital bleeding and spontaneous miscarriage in the first 6 to 8 weeks of gestation if left untreated (Non Patent Literatures 5 and 6).

CITATION LIST

Non Patent Literature

Non Patent Literature 1: Semin Thromb Hemost 2009; 35: 468-77
Non Patent Literature 2: Immunol Lett 2008; 118: 116-24
Non Patent Literature 3: J Thromb Haemost 2011; 9: 1200-6
Non Patent Literature 4: N Engl J Med 1992; 327: 1729-33
Non Patent Literature 5: Curr Drug Targets 2005; 6: 535-9
Non Patent Literature 6: Obstet Gynecol Sury 2007; 62: 255-60

SUMMARY OF INVENTION

Technical Problem

An object of the present invention is to provide a novel convenient and highly accurate method for diagnosing subchorionic hematoma and a method for treating subchorionic hematoma, and to prevent preterm delivery due to subchorionic hematoma by the early diagnosis of the degree of risk for preterm delivery and miscarriage attributed to subchorionic hematoma according to these methods.

Solution to Problem

The present inventors have found that: a PAI-1-deficient patient develops subchorionic hematoma and subchorionic hematoma when pregnant, resulting in miscarriage; and the administration of fresh frozen plasma containing PAI-1 to this patient arrests the progression of the subchorionic hematoma and enables her pregnancy to be maintained (Thrombosis Research 129: 4, e161-e163). Based on these findings, the present inventors have further found that a risk for pregnancy wastage attributed to subchorionic hematoma can be assessed on the basis of PAI activity, leading to the completion of the present invention.

Specifically, the present invention provides the following [1] to [14]:

[1]
A method for diagnosing the degree of risk for preterm delivery or miscarriage, comprising measuring plasminogen activator inhibitor activity or level in plasma isolated from a test subject.

[2]
The method according to [1], wherein the plasminogen activator inhibitor activity in plasma is measured with a euglobulin lysis time as an index.

[3]
The method according to [2], wherein the degree of risk for preterm delivery or miscarriage is determined to be high when the euglobulin lysis time is 500 minutes or shorter.

[4]
The method according to [2] or [3], wherein the degree of risk for preterm delivery or miscarriage is determined to be high when the euglobulin lysis time is 350 minutes or shorter.

[5]
The method according to any of [2] to [4], further comprising the steps of: adding calcium to the plasma and measuring the euglobulin lysis time; and determining a ratio between the euglobulin lysis time in the absence of calcium and the euglobulin lysis time in the presence of calcium, wherein the degree of risk for preterm delivery or miscarriage is determined to be high on the basis of the ratio.

[6]
The method according to [1], wherein the plasminogen activator inhibitor level in plasma is measured by an immunological assay method using an antibody binding to plasminogen activator inhibitor-1.

[7]
The method according to [6], wherein the plasminogen activator inhibitor level in plasma is measured by ELISA.

[8]

The method according to [6], wherein the plasminogen activator inhibitor level in plasma is measured by AlphaLISA.

[9]

The method according to any of [1] to [8], wherein the preterm delivery or the miscarriage is preterm delivery or miscarriage attributed to subchorionic hematoma.

[10]

A kit for the diagnosis of the degree of risk for preterm delivery or miscarriage, comprising α-thrombin, and an aqueous solution containing a calcium ion or kaolin.

[11]

A kit for the diagnosis of the degree of risk for preterm delivery or miscarriage, comprising an antibody binding to plasminogen activator inhibitor-1.

[12]

The kit according to [10] or [11], wherein the preterm delivery or the miscarriage is attributed to subchorionic hematoma.

[13]

A pharmaceutical composition for the prevention of preterm delivery or miscarriage, comprising plasminogen activator inhibitor-1.

[14]

The pharmaceutical composition according to [13], wherein the preterm delivery or the miscarriage is preterm delivery or miscarriage attributed to subchorionic hematoma.

Advantageous Effects of Invention

Use of the present invention allows for hematological and quantitative diagnosis of subchorionic hematoma, which has heretofore been diagnosed only by diagnostic imaging based on ultrasonic tomography, and the degree of risk for preterm delivery or miscarriage; therefore, the degree of risk for preterm delivery or miscarriage can be diagnosed early with improved diagnostic accuracy. According to the present invention, pregnancy can be maintained to prevent pregnancy wastage, even if subchorionic hematoma occurs.

BRIEF DESCRIPTION OF DRAWING

FIG. 1 shows the amount of genital bleeding (G.B.) (g), fresh frozen plasma (FFP) administered (U: 1 U=plasma separated from 200 mL blood), and plasma D-dimer levels (μg/mL) observed during the course of three pregnancies in a PAI-1-deficient patient. The black arrow indicates the day of the miscarriage. The white arrows indicate when the emergency caesarean sections were performed.

DESCRIPTION OF EMBODIMENTS

1. Definition

"Plasminogen activator inhibitor-1 (PAI-1)" is a member of the serine protease inhibitor (SERPIN) superfamily and is the primary physiological regulator of urokinase type plasminogen activator (uPA) and tissue type plasminogen activator (tPA).

"Plasminogen activator inhibitor-2 (PAI-2)" is a member of the SERPIN superfamily and is a physiological regulator of uPA and tPA. PAI-2 is derived from the placenta and is hardly expressed in non-pregnant states.

In the present invention, "plasminogen activator inhibitor activity", "PAI activity", or "activity of PAI" refers to the activities of inhibiting a fibrinolytic system through the inactivation of plasminogen activator, possessed by PAI-1 and PAI-2, and means the entire amount of the fibrinolysis inhibitory activities possessed by PAI-1 and PAI-2. The fibrinolysis inhibitory activity is composed mainly of PAI-1 activity even in pregnant women, though PAI-2 is also secreted from the placenta during pregnancy. In the present invention, therefore, the PAI activity measured represents activity attributed mainly to PAI-1. In this context, higher plasminogen activator inhibitor activity leads to the stronger inhibition of the fibrinolytic system.

"Subchorionic hematoma" is often found in early to middle gestation and emerges at the decidual-placental interface. This hematoma is characterized by being formed along the placental periphery. Subchorionic hematoma found in early gestation undergoes spontaneous regression in most cases, but may last until middle gestation. Such lasting subchorionic hematoma causes uncontrollable uterine contractions, increased genital bleeding, intrauterine infection, etc., resulting in an increased chance of placental dysfunction or pregnancy wastage.

In the present invention, "preterm delivery" means that a baby is born after 22 weeks of gestation earlier than 37 weeks' gestation. "Miscarriage" refers to a loss of pregnancy earlier than 22 weeks of gestation. In the present specification, preterm delivery and miscarriage are also referred to as "pregnancy wastage".

In the present invention, the "degree of risk for preterm delivery or miscarriage" or the "degree of risk for pregnancy wastage" refers to an examination and assessment criterion for determining whether or not a test subject undergoes pregnancy wastage. A test subject having a higher degree of risk for pregnancy wastage is judged to have a higher chance of getting pregnancy wastage, while a test subject having a lower degree of risk for pregnancy wastage is judged to have a lower chance of getting pregnancy wastage or to be normally pregnant.

2. Method for Assessing Degree of Risk for Preterm Delivery or Miscarriage

The present invention relates to a method for assessing the degree of risk for preterm delivery or miscarriage, comprising measuring plasminogen activator inhibitor activity or levels in plasma.

(1) Isolation of Plasma

An assay sample used in the present invention is plasma prepared from blood collected from a test subject by an ordinary method. The blood collection can be carried out by a method well known in the art. The blood collection method can be appropriately selected by those skilled in the art and is preferably a method using sodium citrate as an anticoagulant that permits favorable preservation of blood coagulation factors. In the present invention, peripheral blood can be used as a sample. A method well known in the art, such as centrifugation, can be used as the plasma preparation method. The plasma thus obtained may be cryopreserved until assay.

(2) Measurement of Plasminogen Activator Inhibitor Activity or Level

In the present invention, the plasminogen activator inhibitor activity can be measured by a method for measuring a euglobulin clot lysis time (ECLT) or a euglobulin lysis time, which is a method well known to those skilled in the art. In this context, the euglobulin clot lysis time refers to assay on the time required for clots formed in a plasma euglobulin fraction to be spontaneously lysed, and reflects the overall fibrinolytic activity of plasma determined mainly by the balance between PAI-1 and tPA. Since plasminogen activator inhibitor-2 is also secreted from the placenta during pregnancy, ECLT results obtained from a pregnant woman represent the entire amount of the activity of the plasminogen activator inhibitor-1 and the activity of the plasminogen activator inhibitor-2 in a narrow sense. The fibrinolysis inhibitory activity, however, is composed mainly of plasminogen activator inhibitor-1 activity even in pregnant women. In the present invention, therefore, the PAI activity measured using ECLT represents activity attributed mainly to PAI-1.

The method for measuring a euglobulin clot lysis time involves removing antiplasmin and measuring the lysis time of fibrin and can be appropriately carried out by those skilled in the art. Specifically, plasma is diluted with an acetate buffer solution and left standing, followed by centrifugation. The precipitates are collected and mixed with Tris buffer solution to obtain a euglobulin fraction. Then, a sample of the euglobulin fraction is added to a solution containing α-thrombin and calcium ions or kaolin. The lysis time of the precipitates is measured. In the present invention, this lysis time is used as an index for PAI activity. A shorter euglobulin clot lysis time represents lower PAI activity, i.e., higher fibrinolytic activity.

In one aspect of the present invention, a ratio is determined between a euglobulin clot lysis time measured without the addition of calcium ions (Regular ECLT) and a euglobulin clot lysis time measured in the presence of added calcium ions (Ca-added ECLT), and this ratio may be used as an index for PAI activity. The euglobulin lysis time in the absence of calcium ions is determined by: adding a euglobulin fraction sample prepared in the same way as above to a solution containing α-thrombin; and measuring the lysis time of the precipitates.

Immunological assay methods using an anti-PAI-1 antibody, which are well known to those skilled in the art, can be used for measuring plasminogen activator inhibitor levels. Specifically, methods can be used, such as Western blotting, immunoprecipitation, enzyme immunoassay (EIA), enzyme-linked immunosorbent assay (ELISA), fluorescence immunoassay (FIA), radioimmunoassay (RIA), and AlphaLISA (registered trademark, PerkinElmer, Inc.).

The AlphaLISA method refers to an assay method using luminescent signals that are detectable only when donor and acceptor beads come into close proximity through the biological interaction between a molecule bound with the donor bead and a molecule bound with the acceptor bead. Specifically, these two beads are brought into close proximity in the presence of an antigen. The laser excitation of the donor bead induces the release of a singlet oxygen molecule, which in turn reacts with a thioxene derivative in the acceptor bead to initiate chemiluminescent reaction. Luminescence energy generated from this reaction is transferred to a fluorescent material present in this acceptor bead to emit light. Accordingly, in the present invention, the PAI-1 levels can be quantified by AlphaLISA using anti-PAI-1 antibody-bound donor and acceptor beads. Alternatively, in the present invention, an anti-PAI-1 antibody and uPA are bound to donor and acceptor beads or acceptor and donor beads, respectively, to prepare anti-PAI-1 antibody-bound donor beads and uPA-bound acceptor beads or uPA-bound donor beads and anti-PAI-1 antibody-bound acceptor beads. These beads may be used in AlphaLISA. In this case, only active PAI-1 in a sample binds to the donor and acceptor beads. As a result, the PAI-1 activity can be measured.

The measurement of the plasminogen activator inhibitor activity or levels is not limited to the methods described above, and any method well known to those skilled in the art can be used as long as the activity or the levels can be measured by the method. Alternatively, two or more of these assay method may be used.

(3) Assessment of Degree of Risk for Pregnancy Wastage

The present inventors have found that: a PAI-1-deficient patient develops subchorionic hematoma when pregnant, resulting in miscarriage; and the administration of fresh frozen plasma containing PAI-1 to this patient arrests the progression of the subchorionic hematoma and enables her pregnancy to be maintained. The present inventors have also revealed that in this patient, the PAI-1 deficiency abnormally activates the fibrinolytic system of blood and reduces the adherence between the egg membrane and the uterine, giving rise to the subchorionic hematoma. Based on these findings, the present inventors have further found that: subchorionic hematoma can be diagnosed on the basis of PAI activity or levels; and a risk for pregnancy wastage attributed to subchorionic hematoma can be assessed on the basis of PAI activity or levels.

Based on these findings, in the present invention, the test subject is determined to have a chance of subchorionic hematoma and to be at high risk for pregnancy wastage, when the plasminogen activator inhibitor activity or levels measured by the method mentioned above are lower than a standard value-standard deviation in a normal pregnant woman.

Specifically, in the case of using a euglobulin clot lysis time as an index, the degree of risk for preterm delivery or miscarriage is determined to be high, when the PAI activity is lower than that in the plasma of a normal pregnant woman, for example, when the euglobulin clot lysis time is approximately 500 minutes or shorter, approximately 400 minutes or shorter, approximately 350 minutes or shorter, or approximately 200 minutes or shorter. In the case of using, as an index, a ratio (regular ECLT/Ca-added ECLT) between an euglobulin clot lysis time measured in the absence of calcium ions (regular ECLT) and euglobulin clot lysis time measured in the presence of calcium ions (Ca-added ECLT), the degree of risk for preterm delivery or miscarriage is determined to be high, for example, when the ratio is approximately 5.0 or lower, approximately 4.0 or lower, approximately 3.0 or lower, or approximately 1.5 or lower.

Alternatively, in the case of using plasminogen activator inhibitor level as an index, the degree of risk for preterm delivery or miscarriage is determined to be high, when the plasminogen activator inhibitor level is lower than those in the plasma of a normal pregnant woman, for example, when the plasminogen activator inhibitor level is less than 0.75 times, less than 0.5 times, less than 0.25 times, or less than 0.1 times those in a normal pregnant woman. In the case of measuring PAI-1 level according to ELISA, the degree of risk for preterm delivery or miscarriage is determined to be high, when the PAI-1 level is, for example, approximately 4 ng/ml or lower, approximately 3 ng/ml or lower, approximately 2 ng/ml or lower, approximately 1.6 ng/ml or lower, or approximately 1 ng/ml or lower. In the case of measuring PAI-1 levels according to AlphaLISA, the degree of risk for preterm delivery or miscarriage is determined to be high, when the PAI-1 level is, for example, approximately 60 ng/ml or lower, approximately 40 ng/ml or lower, approximately 20 ng/ml or lower, or approximately 10 ng/ml or lower.

In the present invention, the degree of risk for pregnancy wastage in a test subject may be assessed on the basis of the PAI-1 activity or levels obtained by one assay method.

Alternatively, the degree of risk for pregnancy wastage in a test subject may be assessed on the basis of the PAI-1 activity or levels obtained by a plurality of assay methods.

3. Kit for Assessment of Degree of Risk for Pregnancy Wastage

The kit according to the present invention can be any kit for carrying out the method for assessing the degree of risk for pregnancy wastage described in the preceding paragraph 2. Specific constitution, materials, instruments, etc. involved in this kit are not particularly limited.

In one aspect of the present invention, the kit of the present invention comprises α-thrombin and an aqueous solution containing a calcium ion (e.g., calcium chloride) or kaolin. The kit of the present invention may further comprise a buffer solution such as an acetate buffer solution, Tris buffer solution, or a phosphate buffer solution. The kit of the present invention may also comprise a blood collection tube containing a sodium citrate buffer solution.

In another aspect of the present invention, the kit of the present invention comprises an antibody directed against plasminogen activator inhibitor-1 (primary antibody). The antibody can be any antibody capable of recognizing plasminogen activator inhibitor-1 and may be a polyclonal antibody or a monoclonal antibody. Alternatively, an antibody fragment, for example, Fab, Fab', or F (ab')2 may be used in some cases. The kit of the present invention may further comprise a solid-phase carrier, a standard, and a secondary antibody. Also, the kit of the present invention may further comprise a standard of plasminogen activator inhibitor-1, a diluent, a buffer solution, and a substrate and a stop solution for the detection reaction of an antigen-antibody complex.

Examples of the solid-phase carrier include carriers made of glass, plastic, natural or modified cellulose, polyacrylamide, agarose, polypropylene, polyethylene, dextran, nylon, amylase, magnetite, or any other suitable material well known to those skilled in the art. The solid-phase carrier may be in the form of, for example, a plate, a well, a slide, beads, particles, a tube, a fiber, or a membrane. Any substance that is available in immunological methods can be used as the standard. Examples thereof include enzymes, fluorescent substances, and luminescent substances. The antibody may be immobilized on the solid-phase carrier.

The kit of the present invention may further comprise, as a secondary antibody, an antibody binding to the antibody directed against plasminogen activator inhibitor-1, or an anti-plasminogen activator inhibitor-1 antibody that recognizes an epitope different from that recognized by the primary antibody. The secondary antibody may be labeled with an enzyme, a radioisotope, a fluorescent dye, avidin, biotin, or the like.

4. Pharmaceutical Composition for Prevention of Pregnancy Wastage, Comprising Plasminogen Activator Inhibitor-1

The pharmaceutical composition of the present invention comprises plasminogen activator inhibitor-1 (PAI-1) as a main ingredient. Alternatively, the pharmaceutical composition of the present invention may comprise variant plasminogen activator inhibitor-1 (variant PAI-1) having activity equivalent to or higher than that of PAI-1, as a main ingredient. In this context, the "equivalent activity" refers to the strength of activity substantially equal to that of the activity of inhibiting a fibrinolytic system through the inactivation of plasminogen activator, possessed by PAI-1. The "variant plasminogen activator inhibitor-1" refers to a variant having the substitution, deletion, addition, or insertion of one or several amino acids in the amino acid sequence of wild-type PAI-1. The term "one or several" refers to an integer of 10 or lower, for example, 1 to approximately 10, preferably 1 to approximately 5.

Also, the pharmaceutical composition of the present invention may further comprise a pharmaceutically acceptable carrier or an additive generally used in the art according to its dosage form as long as the effect of preventing preterm delivery and/or miscarriage is not impaired. The additive that can be contained in the pharmaceutical composition of the present invention can be, for example, a colorant, a preservative, a flavoring agent, a flavor corrective, a taste corrective, a sweetener, or a stabilizer, or any other pharmaceutically acceptable additives.

The contents of all patents and references explicitly cited herein are incorporated herein by reference in their entirety. Also, the contents described in the specification and drawings of Japanese Patent Application No. 2011-249523 (filed on Nov. 15, 2011) based on which the priority of the present application is claimed are incorporated herein by reference in their entirety.

Hereinafter, the present invention will be described further specifically with reference to Examples. However, the present invention is not intended to be limited by these Examples.

EXAMPLES

1. Course of Pregnancies in PAI-1-Deficient Patient (1) First Pregnancy

The patient was a 47-year-old woman who had experienced multiple episodes of major bleeding. The first pregnancy occurred at the age of 26 years. The pregnancy course was uneventful, and foetal growth was normal until 16 weeks' gestation. At the end of 16 weeks' gestation, a small amount of genital bleeding was observed, and the patient was hospitalised. Her prothrombin time, activated partial thromboplastin time, and plasma fibrinogen levels were within the normal limits (13.0 s, 34.9 s, and 165 mg/dL, respectively); however, plasma D-dimer levels were slightly elevated (2.4 µg/mL, a normal range is <0.5 µg/mL). In this context, the D-dimer is a plasmin-mediated fibrin degradation product. D-dimer monitoring is a fibrinolysis analysis method used for clinical pathological states. Fresh frozen plasma (FFP) was injected twice a week to control the genital bleeding and maintain her pregnancy. Plasma D-dimer levels were suddenly elevated at the end of 18 weeks' gestation, and massive genital bleeding was observed at 19 weeks' gestation. Although a retro-placental or peripheral echo-free space was not observed, the foetal heart beat had stopped and the cervix of the patient's uterus was found to be fully opened. Plasma D-dimer levels were decreased, and genital bleeding had stopped 1 week after removal of the foetus (220 g). The aborted foetus was male and his appearance was normal.

(2) Second Pregnancy

The second pregnancy occurred at the age of 27 years. Immediately after the confirmation of pregnancy at 7 weeks' gestation, the patient was admitted to present inventors' hospital. Although a small amount of genital bleeding was observed at 8 weeks' gestation, this pregnancy was uneventful until 11 weeks' gestation. A continuous but small amount of genital bleeding was observed after the end of 11th week of gestation; therefore, FFP administration 2 to 3 times per week was initiated. Although the genital bleeding had stopped at 20 weeks' gestation, FFP administration was continued to stabilize the pregnancy. Because plasma D-dimer levels were slightly elevated at 28 weeks' gestation, the frequency of FFP administration was changed from 2 to 3 times per week to every other day. However, plasma D-dimer levels continued to be elevated, reaching 128 μg/mL at 32 weeks' gestation, accompanied by uncontrollable uterine contractions with abruptio placenta diagnosed by ultrasonography. Hence, an emergency caesarean section was carried out, so that the patient delivered a live 1736-g female infant. Perioperative blood loss amounted to 4500 mL, which was controlled by the administration of 42 U FFP.

(3) Third Pregnancy

The third pregnancy occurred at the age of 29 years. Based on the successful management of the previous pregnancy, the patient was hospitalised at 8 weeks' gestation, and continuous FFP administration was initiated. FFP was administered twice a week until 16 weeks' gestation, which was gradually increased until 19 weeks' gestation. After 20 weeks' gestation, FFP administration was performed every day. Although the pregnancy was stabilized until 24 weeks' gestation, plasma D-dimer levels were continuously elevated from 25 weeks' gestation, reaching 57.9 μg/mL at 27 weeks' gestation, accompanied by uncontrollable uterine contractions with abruptio placenta. Accordingly, an emergency caesarean section was again carried out, so that the patient delivered a live 978-g female infant. Perioperative blood loss amounted to 1037 mL. These two daughters were healthy and did not have any symptoms.

(4) Summary

These results indicated that PAI-1 plays an important role in the maintenance of pregnancy in humans. It may therefore be assumed that low levels of PAI-1 may be a risk factor for spontaneous miscarriage and/or preterm delivery in humans.

2. Measurement of PAI Activity

A. Method for Measuring Euglobulin Clot Lysis Time (1) Method for Measuring PAI Activity The blood of each patient collected in citric acid was centrifuged at 3000 g for 10 minutes to collect a supernatant, which was used as a plasma sample. This plasma was diluted 20-fold with a 10 mM acetate buffer solution (pH 4.5) and left standing at 4° C. for 1 hour. After subsequent centrifugation at 1500 g at 4° C. for 10 minutes, precipitates were collected and mixed with a 0.1 M Tris buffer solution (pH 7.4). This mixture was used as a euglobulin fraction.

A sample (150 μl) of the euglobulin fraction was added to 12.5 U/ml (final concentration) α-thrombin. The lysis time of the precipitates was measured (Regular ECLT). A sample (150 μl) of the euglobulin fraction was added to 2.5 U/ml (final concentration) α-thrombin and a solution containing 10 mM (final concentration) calcium ions. Then, the lysis time of the precipitates was measured (Ca-added ECLT). In this context, kaolin (at the same concentration as that of calcium) may be used instead of the calcium ions.

(2) PAI Activity (Euglobulin Lysis Time)

The PAI activity (Ca-added ECLT) in patients who had experienced threatened preterm delivery or threatened miscarriage due to subchorionic hematoma and normal pregnant women was measured according to the method described in the preceding paragraph (1). The results are summarized in Table 1. The blood was collected from each patient in early gestation (up to 15 weeks).

TABLE 1

| Patient | PAI activity |
|---|---|
| Patient who had experienced threatened preterm delivery due to subchorionic hematoma | 94 min |
| Patient who had experienced threatened miscarriage due to subchorionic hematoma | 181 min |
| Normal pregnant women case 1 | 426 min |
| Normal pregnant women case 2 | 418 min |
| Normal pregnant women case 3 | 462 min |

The PAI-1 activity (euglobulin lysis time) in 7 patients with subchorionic hematoma, of which 4 patients had a history of preterm delivery and/or a history of miscarriage, and 5 normal pregnant women was measured in the same way as the method described in the preceding paragraph (1). The results are summarized in Table 2.

The measurement values of Table 2 represent a euglobulin lysis time (Regular ECLT), a euglobulin lysis time in the presence of calcium (Ca-added ECLT), and an ECLT ratio (Regular ECLT/Ca-added ECLT). The blood was collected from each patient in early gestation (up to 15 weeks).

TABLE 2

| | Due to subchorionic hematoma | | Presence or | | | |
|---|---|---|---|---|---|---|
| | History of miscarriage | History of preterm delivery | absence of subchorionic hematoma | Regular ECLT [min] | Ca-added ECLT [min] | ECLT ratio |
| Case 1 | ○ | ○ | | 125 | 130 | 0.96 |
| Case 2 | ○ | ○ | | 155 | 145 | 1.07 |
| Case 3 | ○ | | ○ | 1090 | 240 | 4.54 |
| Case 4 | | ○ | ○ | 960 | 375 | 2.56 |
| Case 5 | | | ○ | 350 | 170 | 2.06 |
| Case 6 | | | ○ | 1200 | 525 | 2.29 |
| Case 7 | | | ○ | 500 | 290 | 1.72 |
| Pregnant woman A (10 weeks' gestation) | | | | 1200 | 315 | 3.81 |
| Pregnant woman B (28 weeks' gestation) | | | | >1200 | 215 | |
| Pregnant woman C (36 weeks' gestation) | | | | >1200 | 470 | |
| Pregnant woman D (36 weeks' gestation) | | | | >1200 | 910 | |
| Pregnant woman E (36 weeks' gestation) | | | | >1200 | 625 | |

(3) Assay Results

As a result, the cases having histories of miscarriage and/or preterm delivery due to subchorionic hematoma or the cases diagnosed as having subchorionic hematoma at the time of sampling (Cases 1 to 7) showed a tendency for shorter euglobulin lysis time, compared with the cases with the normal pregnancy course.

In general, pregnant women are well known to have an activated coagulation system and an inhibited fibrinolytic system, which contribute to the maintenance of the pregnancy and hemostasis at the time of delivery. It is also known that a tendency for the inhibition of the fibrinolytic system gets stronger with increase in gestational week. The very large values (>1200) of Regular ECLT in the normal pregnancy cases and larger values of Ca-added ECLT with increase in gestational week may reflect this inhibition of fibrinolysis.

By contrast, the Cases 1 to 7 had a relatively short euglobulin lysis time and exhibited a fibrinolysis inhibitory effect smaller than that found in the normal pregnancy cases. Also from short Ca-added ECLT, these cases were presumed to have low activity of PAI-1 and to lack fibrinolysis inhibitory functions.

As seen from the above results, patients having a euglobulin lysis time of 500 minutes or shorter have low PAI-1 activity, are likely to already have subchorionic hematoma, and are considered at risk for preterm delivery or miscarriage. Patients having a euglobulin lysis time of 350 minutes or shorter are considered at high risk for preterm delivery or miscarriage.

Patients having a ratio between a euglobulin lysis time and a lysis time shortened by the addition of calcium (Regular ECLT/Ca-added ECLT) of 4.0 or lower have low PAI-1 activity, are likely to already have subchorionic hematoma, and are considered at risk for preterm delivery or miscarriage. Patients having this ratio of 1.5 or lower are considered at high risk for preterm delivery or miscarriage.

B. ELISA (1) Method for Measuring PAI Activity

The blood of each patient collected in citric acid was centrifuged at 3000 g for 10 minutes to collect a supernatant, which was used as a plasma sample. PAI-1 levels (antigen levels) were measured as described below using human Serpin E1/PAI-1 DuoSet Kit (R&D Systems, Inc.).

A capture antibody (mouse-derived anti-human Serpin E1 antibody) was diluted to 4 µg/mL with a phosphate-buffered saline. Each well of a microplate was coated with this capture antibody. Recombinant human Serpin E1 attached to the kit was diluted to 20 ng/mL to 0.3125 ng/mL with phosphate-buffered saline containing 1% bovine serum albumin (hereinafter, referred to as R.D.) to prepare PAI-1 standard solutions. 100 µL of these standard solutions and the plasma sample of each patient were added dropwise to the each well of the capture antibody-coated microplate and left standing at room temperature for 2 hours. Then, each well was washed three times with a washing buffer. A biotinylated goat-derived anti-human Serpin E1 antibody attached to the kit was diluted with R.D. and heat-treated. Then, 2% normal goat serum was added thereto to prepare a 400 ng/mL detection antibody solution. 100 µL of this detection antibody solution was added dropwise to the each well and left standing at room temperature for 2 hours. Then, each well was washed three times with a washing buffer. 100 µL of a streptavidin-conjugated HRP solution was added dropwise to the each well and left standing at room temperature for 20 minutes with light shielded. Then, each well was washed three times with a washing buffer. Then, the chromogenic reaction of the plate was performed for 20 minutes and terminated by the addition of a reaction stop solution. Absorbance was measured at a wavelength of 450 nm using a microplate reader, while a wavelength of 540 nm was filtered out. A calibration curve of PAI-1 levels was prepared from the known levels of the PAI-1 standard solutions and the absorbance. The PAI-1 levels of the plasma sample were calculated.

(2) PAI Activity (PAI-1 Levels)

The PAI-1 levels (antigen levels) in patients who had experienced preterm delivery and/or miscarriage due to subchorionic hematoma and normal pregnant women were measured according to the method described in the preceding paragraph (1). The results are summarized in Table 3. The blood was collected from each patient in early gestation (up to 15 weeks). Case 1 represents a PAI-1-deficient patient.

TABLE 3

| | Due to subchorionic hematoma | | Presence or absence of subchorionic hematoma | PAI-1 level [ng/mL] |
|---|---|---|---|---|
| | History of miscarriage | History of preterm delivery | | |
| Case 1 | O | O | | 0.00 |
| Case 2 | O | O | | 1.53 |
| Case 3 | O | | O | 0.23 |
| Case 4 | | O | O | 1.12 |
| Case 5 | | | O | 1.82 |
| Case 6 | | | O | 0.60 |
| Case 7 | | | O | 1.52 |
| Normal pregnant woman F (10 weeks' gestation) | | | | 5.15 |
| Normal pregnant woman G (20 weeks' gestation) | | | | 4.73 |
| Non-pregnant woman A | | | | 1.51 |
| Non-pregnant woman B | | | | 0.90 |

(3) Assay Results

As a result, the cases having histories of miscarriage and/or preterm delivery due to subchorionic hematoma or the cases diagnosed as having subchorionic hematoma at the time of sampling (the Cases 1 to 7) showed a tendency for lower PAI-1 levels measured by ELISA, compared with the cases with the normal pregnancy course.

As seen from the above results, patients having PAI-1 levels (antigen levels) of 4 ng/ml or lower measured by use of ELISA have low PAI-1 activity, are likely to already have subchorionic hematoma, and are considered at risk for preterm delivery or miscarriage. Patients having PAI-1 levels (antigen levels) of 1.6 ng/ml or lower are considered at very high risk for preterm delivery or miscarriage.

C. AlphaLISA (1) Method for Measuring PAI Activity

AlphaLISA is a method for measuring levels using streptavidin donor beads bound with a biotinylated anti-PAI-1 antibody and AlphaLISA acceptor beads chemically bound with an anti-PAI-1 antibody. When PAI-1 binds to both of the beads, these two beads come into close proximity. Upon irradiation with 680 nm excitation light, a photosensitive substance in the donor bead brings ambient oxygen into a singlet excited state and causes chemical reaction in the acceptor bead located close thereto, resulting in detectable luminescence with a wavelength of 615 nm. Luminescent signals are proportional to the amount of PAI-1 in a sample; therefore, the PAI-1 levels can be quantified by analysis using a calibration curve.

The blood of each patient collected in citric acid was centrifuged at 3000 g for 10 minutes to collect a supernatant, which was used as a plasma sample. PAI-1 levels in this plasma were measured as described below using AlphaLISA Human Plasminogen Activator Inhibitor-1 (PAI-1) Kit (PerkinElmer, Inc.).

AlphaLISA human PAI-1 attached to the kit was diluted to 1000 ng/mL to 0.003 ng/mL with fetal bovine serum to prepare PAI-1 standard solutions. Also, the plasma sample of each patient was diluted with 2-fold with fetal bovine serum. 5 µL of the PAI-1 standard solutions and the plasma sample thus diluted were added dropwise to each well of a microplate. 10 µL of AlphaLISA Anti-PAI-1 Acceptor beads (final concentration: 10 µg/mL) were further added dropwise to each well of the microplate and left standing at 23° C. for 30 minutes. Then, 10 µL of Biotinylated Antibody Anti-PAI-1 (final concentration: 1 nM) was added dropwise to each well of the microplate and left standing for 60 minutes. Finally, 25 µL of Streptavidin-coated Donor beads (final concentration: 40 µg/mL) were added dropwise to each well of the microplate and left standing at 23° C. for 30 minutes with light shielded. Then, 615 nm luminescent signals detected upon irradiation with 680 nm excitation light were obtained. A calibration curve of PAI-1 levels was prepared on the basis of the luminescent signals from the PAI-1 standard solutions. The PAI-1 levels of the plasma sample were calculated.

(2) PAI Activity (PAI-1 Levels)

The PAI-1 levels (antigen levels) in 2 patients who have experienced preterm delivery and/or miscarriage due to subchorionic hematoma, 2 normal pregnant women, and 2 non-pregnant women were measured according to the method described in the preceding paragraph (1). The results are summarized in Table 4. The blood was collected from each patient in early gestation (up to 20 weeks). Case 1 represents a PAI-1-deficient patient.

TABLE 4

| | Due to subchorionic hematoma | | Presence or absence of subchorionic hematoma | PAI-1 level [ng/mL] |
|---|---|---|---|---|
| | History of miscarriage | History of preterm delivery | | |
| Case 1 | ○ | ○ | | 0.06 |
| Case 4 | | ○ | ○ | 23.57 |
| Normal pregnant woman H (15 weeks' gestation) | | | | 129.24 |
| Normal pregnant woman I (20 weeks' gestation) | | | | 94.44 |
| Non-pregnant woman C | | | | 22.30 |
| Non-pregnant woman D | | | | 18.28 |

(3) Assay Results

As a result, the pregnant women were shown to have higher PAI-1 levels, compared with the non-pregnant women, whereas the cases that had experienced miscarriage and/or preterm delivery due to subchorionic hematoma were shown to have evidently low PAI-1 levels. As seen from the above results, patients having PAI-1 levels (antigen levels) of 60 ng/mL or lower measured by use of AlphaLISA have low PAI-1 activity, are likely to already have subchorionic hematoma, and are considered at risk for preterm delivery or miscarriage. Patients having PAI-1 levels (antigen levels) of 20 ng/mL or lower are considered at very high risk for preterm delivery or miscarriage.

(4) Modification of AlphaLISA

In a modified method for measuring PAI-1 levels by AlphaLISA using biotinylated uPA instead of the biotinylated anti-PAI-1 antibody, only active PAI-1 in a sample binds to two beads (donor and acceptor beads). As a result, the PAI-1 activity can be measured. Use of this method allows for more highly sensitive measurement of PAI-1 activity and is probably useful in the early detection of miscarriage or preterm delivery attributed to subchorionic hematoma, as in other assay methods described above.

D. Summary

All the above results of the method for measuring a euglobulin lysis time and the methods for measuring PAI-1 antigen levels demonstrated that: PAI activity correlates with pregnancy wastage caused by subchorionic hematoma; and a patient having PAI activity lower than that in a normal pregnant woman has an activated fibrinolytic system and is therefore susceptible to pregnancy wastage attributed to subchorionic hematoma.

The results of this study produce the difference in the measurement values of PAI-1 levels between ELISA and AlphaLISA. This may be partly because: the different assay methods have their distinct ranges that yield favorable sensitivity (measurable ranges); calibration curves used in the measurement are different therebetween; and the same antibody is not used in the immunological approaches. Human Serpin E1/PAI-1 DuoSet Kit (R&D Systems, Inc.) used in this measurement by ELISA has a measurement area of 2 ng/ml or higher PAI-1 levels. All the measurement results of the case samples used in this study fell outside the area.

Nonetheless, all of the assay methods consistently indicated the correlation between PAI-1 activity and pregnancy wastage caused by subchorionic hematoma; therefore, the measurement of PAI activity or levels probably serves as an examination useful in predicting pregnancy wastage caused by subchorionic hematoma.

In Examples, the method for assessing the degree of risk for preterm delivery or miscarriage according to the present invention is exemplified by methods for assessing the degree of risk for preterm delivery or miscarriage, comprising evaluating PAI-1 activity on the basis of a euglobulin clot lysis time, a ratio between a euglobulin clot lysis time in the absence of Ca and a euglobulin clot lysis time in the presence of Ca, PAI-1 levels measured by ELISA, and PAI-1 levels measured by AlphaLISA. However, the method of the present invention is not limited to the methods described above, and any method capable of measuring PAI-1 activity or levels in pregnant women can be used.

In addition, the assessment in the method for assessing the degree of risk for preterm delivery or miscarriage may be performed on the basis of the PAI-1 activity obtained by one of the assay methods described above or may be performed on the basis of the PAI-1 activity obtained by two or more of the assay methods.

INDUSTRIAL APPLICABILITY

Use of the present invention allows for hematological diagnosis of subchorionic hematoma, which has heretofore been diagnosed only by diagnostic imaging based on ultrasonic tomography; therefore, early diagnosis can be achieved with improved diagnostic accuracy. By use of the present invention, pregnancy can be maintained to prevent pregnancy wastage, even if subchorionic hematoma occurs.

What is claimed is:

1. A method for diagnosing a risk for preterm delivery or miscarriage in a pregnant woman treating the pregnant woman who has been determined to have the risk, comprising the steps of:
   measuring plasminogen activator inhibitor-1 activity or level in plasma isolated from a pregnant woman;
   determining that the pregnant woman has a risk for preterm delivery or miscarriage when the activity or the level is lower than that in the plasma of a normal pregnant woman; and
   administering plasminogen activator inhibitor-1 to the pregnant woman who has been determined to have the risk.

2. The method according to claim 1, wherein the plasminogen activator inhibitor-1 activity in plasma is measured with a euglobulin lysis time as an index.

3. The method according to claim 2, wherein the risk for preterm delivery or miscarriage is determined when the euglobulin lysis time is 500 minutes or shorter.

4. The method according to claim 2, wherein the risk for preterm delivery or miscarriage is determined when the euglobulin lysis time is 350 minutes or shorter.

5. The method according to claim 2, further comprising the steps of:
   adding calcium to the plasma and measuring the euglobulin lysis time; and
   determining a ratio between the euglobulin lysis time in the absence of calcium and the euglobulin lysis time in the presence of calcium,
   wherein the risk for preterm delivery or miscarriage is determined on the basis of the ratio.

6. The method according to claim 1, wherein the plasminogen activator inhibitor-1 level in plasma is measured by an immunological assay method using an antibody binding to plasminogen activator inhibitor-1.

7. The method according to claim 6, wherein the plasminogen activator inhibitor-1 level in plasma is measured by ELISA.

8. The method according to claim 6, wherein the plasminogen activator inhibitor-1 level in plasma is measured by AlphaLISA.

9. The method according to claim 1, wherein the preterm delivery or the miscarriage is preterm delivery or miscarriage attributed to subchorionic hematoma or abruptio placenta.

10. The method according to claim 8, wherein anti-PAI-1 antibody-bound donor beads and uPA-bound acceptor beads, or uPA-bound donor beads and anti-PAI-1 antibody-bound acceptor beads, are used in AlphaLISA.

11. The method according to claim 10, wherein uPA-bound donor beads and anti-PAI-1 antibody-bound acceptor beads are used in AlphaLISA.

* * * * *

UNITED STATES PATENT AND TRADEMARK OFFICE
CERTIFICATE OF CORRECTION

PATENT NO. : 9,448,234 B2
APPLICATION NO. : 14/358116
DATED : September 20, 2016
INVENTOR(S) : Kanayama et al.

Page 1 of 1

It is certified that error appears in the above-identified patent and that said Letters Patent is hereby corrected as shown below:

In the Claims

Column 15, Line 6: the text "woman treating" should read --woman and treating--

Signed and Sealed this
Twenty-first Day of February, 2017

Michelle K. Lee
*Director of the United States Patent and Trademark Office*